United States Patent [19]
Casensky et al.

[11] 3,983,150

[45] Sept. 28, 1976

[54] METHOD OF MANUFACTURE OF N-ALKYLIMINOALANES

[75] Inventors: Bohuslav Casensky, Prague; Jiri Machacek, Rozroky; Tomas Hanslik, Prague, all of Czechoslovakia

[73] Assignee: Ceskoslovenska akademie ved, Prague, Czechoslovakia

[22] Filed: Mar. 26, 1975

[21] Appl. No.: 562,359

[30] Foreign Application Priority Data

Mar. 28, 1974 Czechoslovakia ................. 2250-74

[52] U.S. Cl. ............................................ 260/448 R
[51] Int. Cl.² ........................................... C07F 5/06
[58] Field of Search ................................ 260/448 R

[56] References Cited
UNITED STATES PATENTS 3,651,064    3/1972    Nelson et al. ................... 260/448 R

OTHER PUBLICATIONS

Ehrlich et al., Inorganic Chemistry, vol. 3 No. 5, (1964), pp. 628–631.
Ashby et al., Inorganic Chemistry, vol. 2, No. 3, pp. 499–504, (1963).
Ashby et al., Inorganic Chemistry, vol. 5, No. 9, pp. 1615–1617, (1966).
Laubengayer et al., J.A.C.S. vol. 83, pp. 542–546, (1961).
Laubengayer et al., Inorganic Chemistry, vol. 1, No. 3, pp. 632–637, (1962).

*Primary Examiner*—Helen M. S. Sneed

[57] ABSTRACT

A method of producing of N-alkyliminoalanes by reaction of primary amines, aluminum and hydrogen at high temperature and pressure and in the presence of an initiator.

8 Claims, No Drawings

METHOD OF MANUFACTURE OF N-ALKYLIMINOALANES

The object of the invention is a method of manufacturing N-alkyliminoalanes. More particularly, the invention relates to the direct synthesis whereby N-alkyliminoalanes of the general formula HA1NR are obtained, where R is a straight or branched alkyl with 2 to 6 carbon atoms.

The reaction of aluminium hydride diethyl etherate or trialkylaminate with primary amines or aluminium triamides yielding N-alkyliminoalanes is generally known. The preparation of N-alkyliminoalanes from lithium tetrahydroaluminate and primary amine hydrochlorides was described by E. Wiberg et al in Z. Naturforsch. 10 b(1955), 232, by E. Ehrlich et al. in Inorg. Chem., 3 (1964) 628, and by A. Mazzei et al. in Makromol. Chem., (1969) 122, 168. N-alkyliminoalanes prepared in this way may be used according to U.S. Pat. Nos. 3,245,976 and 3,311,604 as co-catalysts for the polymerization of diolefins.

The common feature of all procedures described above is the fact that the necessary hydride hydrogen is introduced into the reaction in the form of a hydride prepared in advance e.g. by a multistage synthesis. The hydride prepared in this way then reacts with the acidic hydrogen of primary amines or their derivatives.

The drawback of these procedures is the fact that in the optimum case a maximum of 50 percent by weight of the hydride hydrogen may be utilized and additional losses arise during the isolation of the final product.

In accordance with the invention, there is provided a method of manufacturing N-alkyliminoalanes that does not exhibit the aforesaid drawbacks, and that yields the mentioned product in a technologically and economically more advantageous way.

Such method produces N-alkyliminoalanes of the general formula HA1NR, where R represents a straight or branched alkyl with 2 to 6 carbon atoms, and wherein primary amines of the general formula $RNH_2$, where R has the same meaning as mentioned above, are reacted in an organic solvent at a temperature between 70° and 240°C.

In the method of the invention, primary amine, aluminium and hydrogen react together at a pressure in the range from 20 to 500 atomospheres in the presence of an initiator. The initiator may be an alkali metal, preferably sodium, or a complex compound of aluminium hydride and alkali metal hydride or aluminium hydride and Lewis' bases, e.g. trialkyl aminoalane, or aluminium hydride substituted by two alkyls with 1 to 4 carbon atoms, or aluminium hydride substituted with an alkyl iminogroup. Isopropylamine may serve as the primary amine and the reaction may be accomplished in a benzene medium at a temperature in the range from 150° to 200°C, a part of the reaction mixture from the preceding reaction being utilized as the initiator.

The invention is based on the fact that N-alkyliminoalanes ma be obtained in this way in a single-stage process by the direct synthesis of elements and amines. The proper reaction proceeds in two phases: (1) In the first phase, hydrogen is generated by the reaction of amines with metals present in the reaction mixture; (2) In the second phase, when hydrogen is consumed, N-alkyliminoalane is formed in the form of a solution in a organic solvent from which it may be separated by crystallization. As the by-products of the reaction, i.e. alkali hydrides or complex aluminium alkali hydrides, are insoluble in the aforementioned medium, they may be easily separated together with the non-reacted metals, e.g. by means of filtration.

In comparison with prior known methods of the manufacture of N-alkyliminoalanes, the advantage of the procedure accomplished according to this invention consists in the fact tha N-alkyliminoalanes are immediately manufactured in an easily accessible device from the initial raw materials. As the needed hydride hydrogen is generated in this reaction, it need not be added as the initial material, and no losses caused by means of the destruction of the material in the reaction result. The final product is obtained in the form of a concentrated solution and may be used immediately in production.

The advantages of the method of the invention are evident from the following examples that illustrate the principle of the invention without limiting it in any way.

EXAMPLE 1

4.6 g (0.2 mole) of sodium, 17.7g (0.3 mole) of isopropylamine, 10.8g of aluminium with the surface area of 1.37 m$^2$/g, and 40 ml of benzene were placed in a shaking autoclave having a volume of 200 ml and containing 3 steel balls with the diameter of 1.2 cm. The autoclave was then filled with hydrogen to a pressure of 130 atmospheres and heated to a temperature in the range from 155° to 160°C, which led within 90 minutes to a pressure increase of 32 atmospheres (recalculated to 0°C). Simultaneously, the decrease in the content of hydrogen above the mixture resulting from its consumption was observed; within 6 hours the pressure decreased by 25 atmospheres. The autoclave was then cooled and de-aerated. The reaction mixture was then diluted with 80 ml of benzene and transferred into an extraction vessel.

After triplex extraction, 108.5 g of colorless solution was obtained containing 6.86 percent by weight of aluminium, 0.259 percent by weight of H$^-$, 3.69 percent by weight of nitrogen, and 0.13 percent by weight of sodium. The atomic ratio of aluminum : hydrogen : nitrogen : sodium was 1 : 1.01 : 1.036 : 0.022. The yield recalculated to isopropylamine was 95.3%. The residue on the fritted glass filter was dried and 7.9 g of a grey powdered substance was obtained containing 55.81 percent by weight of sodium and 0.21 percent by weight of nitrogen. X-ray analysis of the final product revealed the presence of aluminium, sodium hydride, and small amounts of trisodium aluminium hexahydride.

EXAMPLE 2

50 ml of 10% N-isopropyliminoalane solution in benzene, 69 g of sodium, 220 g of powdered aluminium with the surface area of 0.1 m$^2$/g, 265 g of isopropylamine, and 300 ml of benzene were placed into a 2.5 liter rotary autoclave containing a steel rod weighing 1.5 kg. The autoclave was then closed, filled with hydrogen to the pressure of 130 atmospheres, and heated for 3 hours at a temperature in the range of 130° to 200°C. After this time period, the pressure rose to 260 atmospheres at 200°C. The heating was moderated and the temperature was held constant for the next 5 hours in the range from 150° to 170°C until the pressure remained constant and reached the value of 135 atmospheres after cooling the vessel. The content of the autoclave was then diluted with benzene to the total volume of 1.5 liter and introduced into a glass device, where the fraction soluble in benzene was extracted and allowed to crystallize. 345 g of white crystals of N-isopropyliminoalane were obtained in this manner, such compound having the chemical formula /AlHNCH(CH$_3$)$_2$/$_6$, the yield recalculated to the initial isopropyl amine being 89.4%. The solid residue contained a mixture of sodium, aluminium, sodium hydride, and trisodium aluminium hexahydride.

EXAMPLE 3

50 g of sodium, 200 g of powdered aluminium, 260 g of N-propylamine, 400 ml of benzene, and 50 ml of 10% solution of diisobutyl aluminium hydride in benzene were placed in a rotary autoclave having a capacity of 2.5 liter and containing a mixing rod. The autoclave was filled with hydrogen up to the pressure of 20 atomospheres, was heated for 5 hours at a temperature in the range from 130° to 160°C, after which the vessel was cooled and the pressure raised to 350 atmospheres. The vessel was then heated for 5 hours at a temperature in the range from 130° to 160°C at a pressure of 500 atmospheres, when the hydrogenization proceeds. After cooling the autoclave, the dense slurry was taken out and the fraction soluble in benzene was isolated; this contained 325 g of N-propyliminoalane, which corresponds to the yield of 86.2% recalculated to amine taken into the reaction. The residual solid fraction contains a mixture of aluminium, sodium and sodium hydride.

EXAMPLE 4

0.46 g (0.02 mole) of sodium, 14.6 g (0.2 mole) of tert. butylamine, 9.5 g of aluminium with a surface area of 1.37 m$^2$/g, 0.2 g of sodium aluminium tetrahydride, and 30 ml of benzene were placed in a shaking autoclave having a capacity of 200 ml and containing 3 steel balls with a diameter of 1.2 cm. The autoclave was filled with hydrogen up to the pressure of 138 atomospheres, and heated to the temperature in the range from 155° to 165°C, which led during 3 hours to the pressure rise by 14.8 atmospheres (recalculated to 0°C). As a result of the consumption of hydrogen during the following 7 hours, the pressure decreased by 7.6 atmospheres. The autoclave was cooled, its content diluted with 40 ml of benzene and transferred into an extraction vessel. After the extraction, 75.1 g of colorless solution was obtained, containing 6.48 percent by weight of aluminium, 0.264 percent by weight of H$^-$, 3.65 percent by weight of nitrogen, and 0.024 percent by weight of sodium as determined analytically. The ratio of aluminium : hydrogen : nitrogen atoms was 1 : 1.09 : 1.085. The yield recalculated to t-butylamine was 97.9%.

EXAMPLE 5

0.46 g (0.02 mole) of sodium, 14.6 g (0.2 mole) of isobutylamine, 9.5 g of aluminium with a surface area of 1.37 m$^2$/g, 0.2 g of sodium aluminium tetrahydride, and 30 ml of benzene were placed into a shaking autoclave with the volume of 200 ml together with three steel balls of the diameter of 1.2 cm. The autoclave was filled with hydrogen compressed to 140 atomospheres and heated to the temperature in the range between 150° and 165°C. Within 4 hours, the pressure rose by 20 atmospheres (recalculated to 0°C). As a result of the consumption of hydrogen, there was then a decrease of the pressure within a period of 7.5 hours by 11.7 atmospheres. After cooling the autoclave, the reaction mixture was diluted with 85 ml of benzene and transferred into an extraction vessel from which 114.2 g of colorless solution was separated by extraction with the content of 4.67 percent by weight of aluminium, 0.186 percent by weight of H$^-$, 2.44 percent by weight of nitrogen, and 0.058 percent by weight of sodium as determined analytically; the ratio of the aluminium : hydrogen : nitrogen atoms was 1 : 1.06 : 1. The yield calculated with respect to the initial isobutylamine is 98.7%.

EXAMPLE 6

100 g of an aluminium alloy chips containing the addition of 20 percent by weight of silicon, 5 g of bis (trimethylamino) aluminium hydride, and 500 ml of heptane were placed in a rotary autoclave having a capacity of 2.5 liter together with 2 kg of steel balls of the diameter of 5 – 7 mm. The mixture was milled under an inert atmosphere until the surface of the solid phase equalled 0.5 m$^2$/g; 23 g (1 mole) of sodium and 174 g (2 mole) of 2-aminopentane were added. The autoclave was filled with hydrogen to the pressure of 150 atmospheres and then heating was effected under continuous rotation first for 3 hours at the temperature in the range of 200° to 230°C, and then for 4 hours at a temperature in the range from 140° to 160°C. When the pressure became constant, the autoclave was cooled, the reaction mixture was taken out and extracted with heptane. After the crystallization and evaporation of the mother liquor, 212 g of N-amyl-2-iminoalane (1.87 mole) was obtained, which corresponds to a yield of 93.5%.

EXAMPLE 7

3.9 g of potassium, 3 ml of 10% benzene solution of N-isopropyliminoalane, 27 ml of benzene, 10.8 g of powdered aluminium with the surface area of 1.37 m$^2$/g, and 11.8 g of isopropylamine were placed in a shaking autoclave together with three steel balls of the diameter of 1.2 cm. The autoclave was filled with hydrogen to the pressure of 130 atmospheres and heated to the temperature in the range from 155° to 160°C. After 8 hours' reaction, when the decrease in the pressure of hydrogen stopped, the reaction mixture was diluted with 90 ml of benzene and transferred into an extraction vessel from which 97 g of a clear solution was obtained. Its analysis indicated 4.07 percent by weight of aluminium, 0.148 percent by weight of hydrogen, and 2.13 percent by weight of nitrogen, which corresponds to the atomic ratio of aluminium : hydrogen : nitrogen of 1 : 0.973 : 1.008. The yield of N-isopropyliminoalane was 73.8% with respect to the initial isopropylamine.

EXAMPLE 8

10 ml of 0.8 M solution of bis (trimethylamino) aluminium hydride in toluene, 11.8 g (0.2 mole) of isopropylamine, 20 ml of toluene, and 9.5 g of powdered aluminium with the surface area of 1.37 m$^2$/g were placed in a 200 ml shaking autoclave together with three steel balls of the diameter of 1.2 cm. The autoclave is then filled with hydrogen to the pressure of 130 atmospheres and heated to the temperature in the range from 155° to 160°C; within 1 hour, the pressure increased by 20 atmospheres (recalculated to 0°C). The decrease in hydrogen pressure arising from its consumption in the reaction stopped after 7.5 hours.

After cooling the autoclave, 20 ml of toluene was added to the reaction mixture and the total amount of the mixture was transferred to an extraction vessel from which 49.1 g of clear solution containing 7.96 percent by weight of aluminium, 0.300 percent by weight of H$^{--}$, and 4.46 percent by weight of nitrogen were obtained, the atomic ratio of aluminium : hydrogen : nitrogen being 1 : 1.008 : 1.079. The yield related to isopropylamine equalled 96.9%.

EXAMPLE 9

4.6 g (0.2 mole) of sodium, 11.8 g (0.2 mole) of isopropylamine, 10.8 g of powdered aluminium with the surface area of 1.37 m$^2$/g, and 50 ml of benzene were placed in a shaking autoclave having a capacity of 200 ml together with three steel balls of the diameter of 1.2 cm. The autoclave was then filled with hydrogen to the pressure of 135 atmospheres and heated to a temperature in the range from 150° to 160°C. During a period of 4 hours the pressure rose by 20.3 atmospheres (recalculated to 0°C). After that, the pressure of hydrogen fell by 24.8 atmospheres within 7 hours as a result of its consumption in the reaction. After cooling and opening the autoclave, the reaction mixture was centrifuged and 35.2 g of clear colorless solution was obtained, containing 7.38 percent by weight of aluminium, 0.272 percent by weight of H$^-$, 3.91 percent by weight of nitrogen, and 0.18 percent by weight of sodium. The atomic ratio of aluminium : hydrogen : nitrogen : sodium equalled 1 : 0.986 : 1.02 : 0.028. The reaction residue was transferred to an extraction vessel with a fritted glass filter and 75 ml of benzene was added to it. After extraction, 79.8 g of colorless solution was obtained, containing 2.77 percent by weight of aluminium, 0.107 percent by weight of H$^-$, 1.54 percent by weight of nitrogen, and 0.01 percent by weight of sodium. The atomic ratio of aluminium : hydrogen : nitrogen : sodium was 1 : 1.033 : 1.07 : 0.004. The yield recalculated to the intitial isopropylamine was 93.2 percent by weight.

EXAMPLE 10

200 g of powdered aluminium, 265 g of isopropylamine, 500 ml of benzene, and 70 g of the reaction product prepared as described in Example 9 were placed into a 2.5 liter autoclave together with a mixing rod. The autoclave was filled with hydrogen to the pressure of 140 atmospheres and heated for 7 hours at a temperature in the range from 130° to 220°C, i.e. until the pressure of hydrogen in it was constant. After cooling the autoclave, 350 g of N-isopropyliminoalane was extracted with benzene from the reaction mixture, which corresponded to the yield of 88% recalculated to the initial isopropylamine.

Although the invention is illustrated and described with reference to a plurality of preferred embodiments thereof, it is to be expressly understood that it is in no way limited to the disclosure of such a plurality of embodiments, but is capable of numerous modifications within the scope of the appended claims.

What is claimed is:

1. Method for the preparation of N-alkyliminoalanes of the general formula:

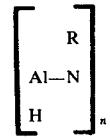

wherein R is an alkyl group having from 2–6 carbon atoms and $n$ is an integer from 4 to 8 which comprises reacting a primary amine of the general formula R—NH$_2$ wherein R is as denoted above, in an organic solvent, with aluminum and hydrogen at a temperature within the range of 70°–240°C at a pressure ranging from 20–500 atmospheres in the presence of an initiator.

2. Method in accordance with claim 1 wherein the initiator is a complex compound of aluminum hydride with a trialkylaminoalane.

3. Method according to claim 1, wherein the initiator is an alkali metal.

4. Method according to claim 3, wherein the initiator is sodium.

5. Method according to claim 1, wherein the initiator is a complex compound of aluminium hydride with alkali metal hydride.

6. Method according to claim 1, wherein the initiator is aluminium hydride substituted with two alkyls with 1 to 4 carbon atoms.

7. Method according to claim 1, wherein the initiator is aluminium hydride substituted with an alkyliminogroup.

8. Method according to claim 1, wherein the primary amine is isopropylamine and the reaction is carried out in benzene medium at a temperature in the range from 150° to 200°C, and wherein the initiator is a part of the reaction mixture from the preceding synthesis.

* * * * *